US00PP18386P2

(12) United States Plant Patent
Delabroye

(10) Patent No.: US PP18,386 P2
(45) Date of Patent: Jan. 1, 2008

(54) ***HEUCHERA* PLANT NAMED 'MOCHA'**

(50) Latin Name: *Heuchera×villosa*
Varietal Denomination: Mocha

(76) Inventor: Sandrine Delabroye, Rue Roger Salengro 40, Hantay (FR), F-59496

( * ) Notice: Subject to any disclaimer, the term of this patent is extended or adjusted under 35 U.S.C. 154(b) by 0 days.

(21) Appl. No.: 11/542,422

(22) Filed: Oct. 3, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Penny J. Aguirre

(57) ABSTRACT

A new cultivar of *Heuchera×villosa,* 'Mocha', characterized by its very dark colored foliage, its large cordate-shaped leaves on rosy red petioles, its compact and mounded plant habit, its tolerance to heat, humidity, and exposure to sunlight, and its hardiness in U.S.D.A. Zones 4 to 9.

2 Drawing Sheets

Botanical classification: *Heuchera×villosa.*
Cultivar designation: 'Mocha'.

BACKGROUND OF THE INVENTION

The present invention relates to a new and distinct cultivar of *Heuchera×villosa,* and is hereinafter referred to by the cultivar name 'Mocha'.

The inventor discovered the new cultivar, 'Mocha', as a naturally whole plant mutation *Heuchera×villosa* in a cultivated nursery bed in Frankrijk, France in summer of 2004. The parent plants of 'Mocha' are unknown, however *Heuchera* 'Brownies' (not patented) and *Heuchera* 'Velvet Night' (not patented) are possible parents based on characteristics and presence in the growing area.

The new cultivar was selected as unique for its large, dark brown colored leaves combined with overall garden performance.

Asexual reproduction of the new cultivar was first accomplished under direction of the inventor by in vitro propagation in Rijswijk, The Netherlands in summer of 2004. Asexual reproduction of the new cultivar by division and tissue culture has shown that the unique features of 'Mocha' are stable and reproduced true to type in successive generations.

SUMMARY OF THE INVENTION

The following traits have been repeatedly observed and represent the characteristics of the new cultivar. These attributes in combination distinguish 'Mocha' as a new and unique cultivar of *Heuchera.*

1. 'Mocha' has foliage that is very dark brown in color. The foliage emerges a coppery brown in spring and changes to dark brown, as it matures. The foliage coloration is sun-fast and retained throughout the growing season.
2. The leaves of 'Mocha' are cordate in shape and larger than in typical for dark foliaged *Heuchera.*
3. 'Mocha' is tolerant to heat, humidity, and exposure to sunlight.
4. The plant habit of 'Mocha' is mounded and compact.

5. 'Mocha' is hardy in U.S.D.A. Zones 4 to 9, hardier than most dark foliaged cultivars of *Heuchera.*

'Mocha' is a unique *Heuchera* with dark color foliage. There are many *Heuchera* cultivars with dark colored foliage, however the combination of having foliage that is this deep in color in combination with its garden performance in a wide range of environmental conditions distinguishes 'Mocha' from all other cultivars known to the inventor.

'Mocha' is most similar to 'Brownies' and 'Velvet Night' in overall characteristics. However, 'Brownies' has lighter brown foliage and 'Velvet Night' is lighter brown with purple mottling and veins. 'Mocha' is similar to *Heuchera villosa* 'Caramel' (U.S. Plant Pat. No. 16,560) in plant habit and foliage characteristics, however 'Caramel' exhibits golden yellow colored foliage.

BRIEF DESCRIPTION OF THE DRAWING

The accompanying colored photographs illustrate the overall appearance and distinct characteristics of the new *Heuchera.* The photographs were taken in The Netherlands of a one year-old plant as grown outdoors in a one gallon container.

The photograph on FIG. 1 provides a view of the spring foliage of new cultivar and the photograph in FIG. 2 is a close-up view of the foliage of 'Mocha'. The colors in the photographs are as close as possible with the photographic and printing technology utilized. The color values cited in the detailed botanical description accurately describe the colors of the new *Heuchera.*

DETAILED BOTANICAL DESCRIPTION OF THE PLANT

Figure 1:
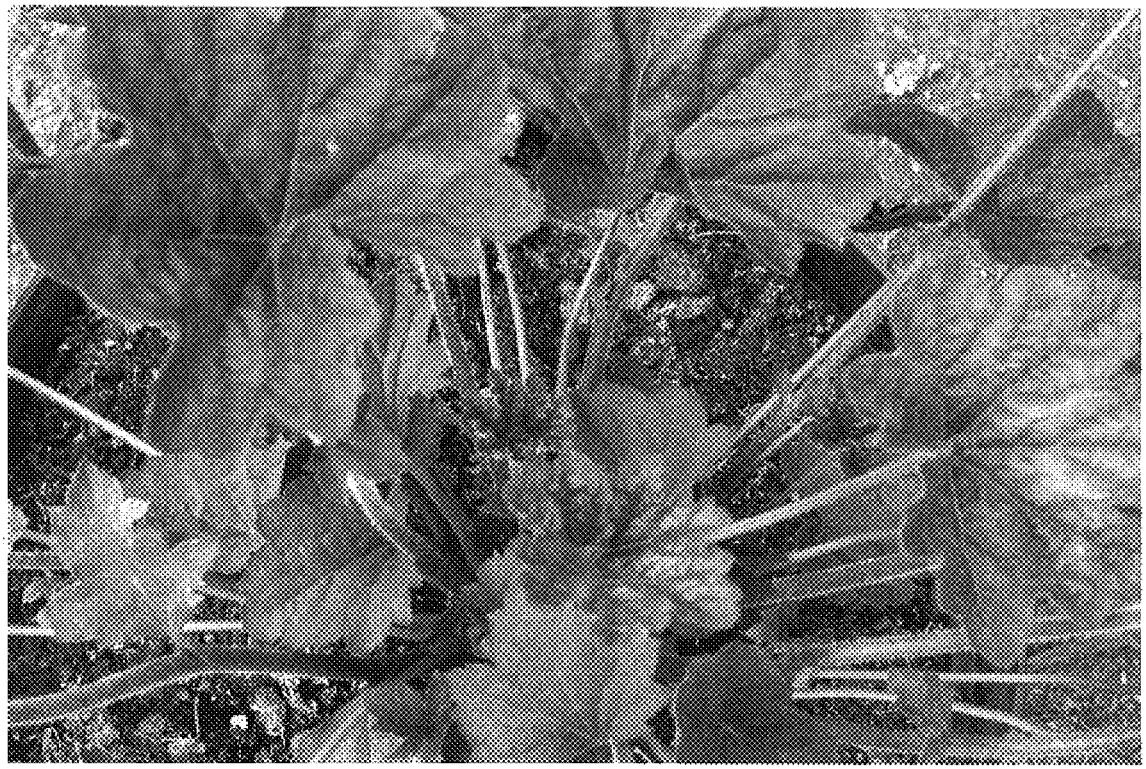
Figure 2:
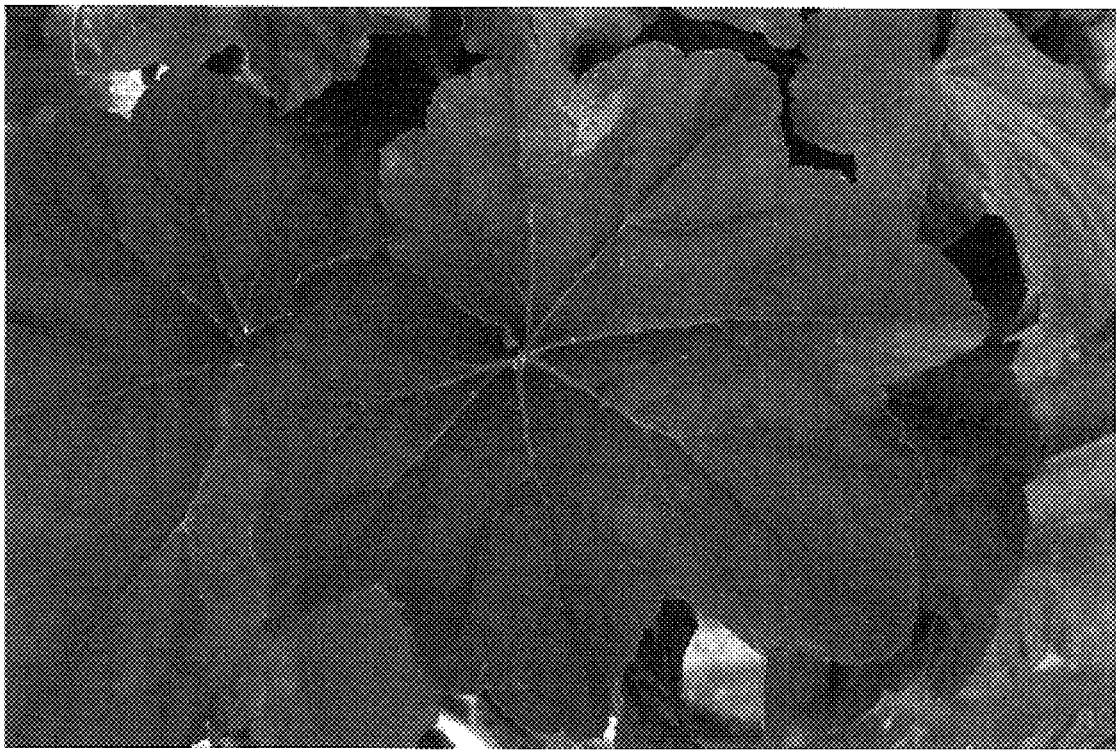

The following is a detailed description of a one year-old plant of the new cultivar as grown outdoors in The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general colors terms of ordinary dictionary significance are used.

Botanical classification: 'Mocha' is a cultivar of *Heuchera*× *villosa.*

General description:

*Plant habit.*—Compact, clump-forming herbaceous perennial, mounded foliage.

*Height and spread.*—Reaches about a height of about 14 cm in height and about 20 cm in width.

*Hardiness.*—U.S.D.A. Zone 4 to 9.

*Culture.*—Full sun to medium shade in moist, well-drained, fertile soils.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method, division are also possible.

*Root initiation.*—Roots appear in rooting media in 10 day at 20° C. in the laboratory without supplemental lighting.

*Root development.*—Rooted transplants from tissue culture fully develop in a 2.5 inch container in about 20 days in a greenhouse with average temperatures of about 20° C. without supplemental lighting in The Netherlands.

*Growth rate.*—Vigorous compared to what is typically observed for *Heuchera* with colored foliage. A 2.5-inch container will fully develop in a one-gallon container in about 2.5 months in the Netherlands.

Foliage description:

*Leaf shape.*—Cordate.

*Leaf division.*—Simple, but lobed with about 5 to 7 lobes per leaf.

*Leaf base.*—Strongly cordate (leaves at base overlap).

*Leaf apex.*—Acute to rounded.

*Leaf venation.*—Primary palmate, secondary net-veined, not conspicuous, vein color on upper surface matched leaf color, vein color on lower surface of mature leaves is N200C.

*Leaf margins.*—Crenate.

*Leaf attachment.*—Petiolate.

*Leaf arrangement.*—Basal rosettes.

*Leaf orientation.*—Held horizontal to petiole, held nearly flat (not ruffled or curled).

*Leaf surface.*—Upper and lower; pubescent with 1 mm stiff white hairs.

*Leaf color.*—Young upper and lower surface; 51B to 51C with markings of N77B to N77C, maturing leaves upper surface; 51C with mottling of N202A, maturing leaves lower surface N79C, mature leaves upper surface; mostly 202B with cast of N189B, mature leaves lower surface; N79C.

*Leaf size.*—Average of 9.5 cm in length and width.

*Leaf quantity.*—About 11 per basal rosette.

*Petiole size.*—Up to 9 cm in length, about 2 mm in width.

*Petiole color.*—182C with standing of N186C, young petioles 145C.

*Petiole shape.*—Round.

*Stipules.*—2 leafy stipules at the base of each petiole, oblong in shape, 1 cm in length, 2 mm in width, color 182C (both surfaces), margins sparsely covered with short hairs.

Flower and seed description: Flowering was been observed under the conditions grown for data collection, creamy white bell-shaped flowers typical of the species should be expected under the right conditions for flowering.

I claim:

1. A new and distinct cultivar of *Heuchera* plant named 'Mocha' as herein illustrated and described.

* * * * *